United States Patent
Dehmer (10) Patent No.: US 10,012,621 B2
(45) Date of Patent: Jul. 3, 2018

(54) SEALED FLUIDIC COMPONENT COMPRISING A COMPOSITE MATERIAL OF DIFFERENT PAEK MATERIALS

(75) Inventor: Bernhard Dehmer, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 384 days.

(21) Appl. No.: 13/996,200

(22) PCT Filed: May 2, 2011

(86) PCT No.: PCT/EP2011/056895
§ 371 (c)(1),
(2), (4) Date: Sep. 11, 2013

(87) PCT Pub. No.: WO2012/084275
PCT Pub. Date: Jun. 28, 2012

(65) Prior Publication Data
US 2013/0341260 A1    Dec. 26, 2013

(30) Foreign Application Priority Data
Dec. 20, 2010   (GB) .................................... 1021505.1

(51) Int. Cl.
*B01L 3/00*     (2006.01)
*G01N 30/60*    (2006.01)
(Continued)

(52) U.S. Cl.
CPC ........ *G01N 30/60* (2013.01); *B01L 3/502715* (2013.01); *F16L 21/00* (2013.01); *G01N 21/05* (2013.01); *G01N 30/6026* (2013.01); *B01L 3/502707* (2013.01); *B01L 2200/0689* (2013.01); *B01L 2300/0654* (2013.01); *B01L 2300/0877* (2013.01); *B29C 65/02* (2013.01); *B29C 65/4815* (2013.01); *B29C 65/5057* (2013.01); *B29C 65/70* (2013.01); *B29C 66/5229* (2013.01); *B29C 66/52231* (2013.01);
(Continued)

(58) Field of Classification Search
None
See application file for complete search history.

(56) References Cited

U.S. PATENT DOCUMENTS

| | | |
|---|---|---|
| 4,982,597 A | 1/1991 | Berger |
| 5,074,599 A | 12/1991 | Wirbel et al. |

(Continued)

FOREIGN PATENT DOCUMENTS

| | | |
|---|---|---|
| CN | 101842855 | 9/2010 |
| EP | 320155 | 11/1988 |

(Continued)

OTHER PUBLICATIONS

Office Action dated Jun. 5, 2015 in European Application No. 11717270.0.
(Continued)

*Primary Examiner* — Katherine Zalasky
*Assistant Examiner* — Kara Graber (57) ABSTRACT

A sealed fluidic component for use in a fluidic flow path is made by providing a composite material comprising a first material and a second material, wherein the first material and the second material are different PAEK materials with the first material having a lower melting point than the second material. The composite material is heated to provide a sealing by the first material.

12 Claims, 5 Drawing Sheets

(51) Int. Cl.
  *G01N 21/05*   (2006.01)
  *F16L 21/00*   (2006.01)
  *B29C 65/02*   (2006.01)
  *B29C 65/50*   (2006.01)
  *B29C 65/70*   (2006.01)
  *B29C 65/00*   (2006.01)
  *G01N 21/03*   (2006.01)
  *B29C 65/48*   (2006.01)
  *G01N 30/74*   (2006.01)

(52) U.S. Cl.
  CPC .. *B29C 66/52241* (2013.01); *B29C 66/52272* (2013.01); *B29C 66/71* (2013.01); *B29C 66/73116* (2013.01); *B29C 66/73776* (2013.01); *B29C 66/919* (2013.01); *B29C 66/91411* (2013.01); *B29C 66/91931* (2013.01); *B29C 66/91933* (2013.01); *B29C 66/91935* (2013.01); *G01N 30/6095* (2013.01); *G01N 30/74* (2013.01); *G01N 2021/0346* (2013.01)

(56) References Cited

U.S. PATENT DOCUMENTS

| | | |
|---|---|---|
| 6,494,500 B1 | 12/2002 | Todosiev et al. |
| 2003/0017305 A1 | 1/2003 | Roitman et al. |
| 2003/0150792 A1 | 8/2003 | Koehler et al. |
| 2007/0097361 A1 | 5/2007 | Beigel et al. |
| 2008/0237112 A1 | 10/2008 | Ford et al. |
| 2009/0117356 A1 | 5/2009 | Hsu et al. |
| 2009/0214386 A1 | 8/2009 | Beigel et al. |

FOREIGN PATENT DOCUMENTS

| | | |
|---|---|---|
| EP | 309596 A1 | 4/1989 |
| EP | 401991 | 6/1989 |
| EP | 1350759 | 10/2003 |
| GB | 2422411 A | 2/2005 |
| WO | WO0044551 | 8/2000 |
| WO | WO0228532 | 4/2002 |
| WO | WO03050035 | 6/2003 |
| WO | WO2005015162 | 2/2005 |
| WO | WO2005084337 | 9/2005 |
| WO | WO2007009492 | 1/2007 |
| WO | WO2008025351 | 3/2008 |
| WO | WO2009088663 A1 | 7/2009 |
| WO | WO2010000324 A1 | 1/2010 |

OTHER PUBLICATIONS

Office Action dated Jun. 26, 2015 in Chinese Application No. 201180061633.8 (Unofficial/Non-certified translation provided by foreign agent included).
W.D. Ehmann, et al. "Heat-Sealed Polyethylene Sample Containers for Neutron Activation Analysis".
John E. Macnair, et al. "Ultrahigh-Pressure Reversed-Phase Liquid Chromatography in Packed Capillary Columns", Anal. Chem. 1997, 69, 983-989.
Office Action dated May 30, 2014 in Chinese Patent Application No. 201180061633.8.
U.K. Examination Report dated Mar. 9, 2017 from related U.K. Application No. GB1021505.1.

SEALED FLUIDIC COMPONENT COMPRISING A COMPOSITE MATERIAL OF DIFFERENT PAEK MATERIALS

The present application is a national stage filing under 35 U.S.C. § 363 of International Patent. Application No. PCT/EP2011/056895 filed on May 2, 2011, naming Valentin Abramzon as inventor. Priority under 35 U.S.C. § 365(c) is claimed from International Patent Application No. PCT/EP2011/056895, and the entire disclosure of International Patent Application No. PCT/EP2011/056895 is specifically incorporated herein by reference. Priority is also claimed from GB1021505 filed on Dec. 20, 2010, the entire disclosure of which is specifically incorporated herein by reference.

BACKGROUND ART

The present invention relates to sealing of fluidic components, in particular in a high performance liquid chromatography application.

In high performance liquid chromatography (HPLC), a liquid has to be provided usually at a very controlled flow rate (e. g. in the range of microliters to milliliters per) and at high pressure (typically 20-100 MPa, 200-1000 bar, and beyond up to currently 200 MPa, 2000 bar) at which compressibility of the liquid becomes noticeable. For liquid separation in an HPLC system, a mobile phase comprising a sample fluid with compounds to be separated is driven through a stationary phase (such as a chromatographic column), thus separating different compounds of the sample fluid which may then be identified.

The mobile phase, for example a solvent, is pumped under high pressure typically through a column of packing medium (also referred to as packing material), and the sample (e.g. a chemical or biological mixture) to be analyzed is injected into the column. As the sample passes through the column with the liquid, the different compounds, each one having a different affinity for the packing medium, move through the column at different speeds. Those compounds having greater affinity for the packing medium move more slowly through the column than those having less affinity, and this speed differential results in the compounds being separated from one another as they pass through the column.

The mobile phase with the separated compounds exits the column and passes through a detector, which identifies the molecules, for example by spectrophotometric absorbance measurements. A two-dimensional plot of the detector measurements against elution time or volume, known as a chromatogram, may be made, and from the chromatogram the compounds may be identified. For each compound, the chromatogram displays a separate curve or "peak". Effective separation of the compounds by the column is advantageous because it provides for measurements yielding well defined peaks having sharp maxima inflection points and narrow base widths, allowing excellent resolution and reliable identification of the mixture constituents. Broad peaks, caused by poor column performance, so called "Internal Band Broadening" or poor system performance, so called "External Band Broadening" are undesirable as they may allow minor components of the mixture to be masked by major components and go unidentified.

During operation, a flow of the mobile phase traverses the column filled with the stationary phase, and due to the physical interaction between the mobile and the stationary phase a separation of different compounds or components may be achieved. In case the mobile phase contains the sample fluid, the separation characteristics are usually adapted in order to separate compounds of such sample fluid. The term compound, as used herein, shall cover compounds which might comprise one or more different components. The stationary phase is subject to a mechanical force generated in particular by a hydraulic pump that pumps the mobile phase usually from an upstream connection of the column to a downstream connection of the column. As a result of flow, depending on the physical properties of the stationary phase and the mobile phase, a relatively high pressure occurs across the column.

The flow path of the mobile phase typically comprises plural individual components coupled together, which, in turn, might also be comprised of individual sub-components. Due to the high pressure applied in most HPLC application, pressure sealing of the components in and along the flow path is required. Further, in case of requirement of biocompatibility, it has to be ensured that all surfaces of components (including conduits) along the flow path that may come in contact with the mobile phase and the sample fluid are comprised of materials generally considered as being biocompatible, i.e., materials that will not release ions (e.g. from metal parts) that may contaminate the sample and/or a column packaging material, and/or adversely affect the analysis itself. Accordingly, proper sealing is required to ensure such biocompatibility.

EP 1910731 A1 discloses coupling of conduits for bringing them in communication. Each of the conduits is adapted for conducting a medium and has an outlet and an outer surface adjacent to the outlet. The outer surfaces and a solid plastic material are at least partly inserted into an aperture of a coupling element. The plastic material is plastified and/or melted at least partly. The plastic material is solidified for sealing and fixing the conduits within the aperture of the coupling element. The coupling element can be part of a flow cell configured for measuring an optical property of a fluid conducted through a fluid conduit.

GB 2422411 A discloses a fluidic terminal for placing one or more fluidic conduits in communication. A conduit for transporting fluid has a proximal end, a distal end, and a substantially cylindrical housing with an axial bore and a proximal face. The proximal end of the conduit is housed within the axial bore with their axes parallel, and the bore is back-filled with a thermoplastic polymer, most preferably PEEK, liquefied and cooled providing for the conduit to breach the sealing face and the thermoplastic to bond the conduit and housing.

Fittings for coupling different components, such as separation columns and conduits, of fluidic devices are commercially available and are offered, for instance, by the company Swagelok (see for instance the website swagelok.com). Typical fittings are disclosed in U.S. Pat. No. 5,074,599 A, U.S. Pat. No. 6,494,500, WO 2005/084337, WO 2009/088663 A1, US 2008/0237112 A1, or WO 2010/000324 A1.

DISCLOSURE

It is an object of the invention to provide an improved sealing of fluidic components, in particular for HPLC applications.

Embodiments according to the present invention comprise a method of providing a sealed fluidic component for use in a fluidic flow path, preferably in an HPLC application. A composite material is provided with that comprises a first material and a second material. Both the first and second materials are polyaryletherketone (PAEK) materials but different from each other, with the first material having a lower melting point than the second material. The composite material is heated in order to provide a sealing by the first material. Such embodiments allow that the second material, with the higher melting point, maintains its shape while the first material, with the lower melting point, provides a sealing, which can be required, for example, to provide a fluid tight sealing in or to the fluidic flow path and/or to provide or ensure biocompatibility.

Polyaryletherketone (PAEK) is a family of semi-crystalline thermoplastics with high-temperature stability and high mechanical strength. PAEK plastics are characterized by phenylene rings that are linked via oxygen bridges (ether and carbonyl groups (ketone)). The ratio and sequence of ether to ketones mainly affects the glass transition temperature and melting point of the polymer. It also affects its heat resistance and processing temperature. The higher the ratio of ketones the more rigid the polymer chain, which results in a higher glass transition temperature and melting point. The processing temperatures can range from 350 to 430° C. Members of the PAEK family include: polyetherketone (PEK), polyetheretherketone (PEEK), polyetherketoneketone (PEKK), polyetheretherketoneketone (PEEKK), and polyetherketoneetherketoneketone (PEKEKK).

Polymers of the PAEK family offer a relatively high adhesion behavior to each other, e.g. as apparent from high surface tension (e.g. according to the VAN OSS method 44.2 mN/m in comparison to PTFE with 18.3 mN/m). With the first and second materials being of the PAEK family, a tight connection along the area of contact can be achieved, thus allowing for high sealing characteristics. Further, polymers of the PAEK family are well accepted for HPLC applications (e.g. HPLC equipment) and compatible with most HPLC mobile phases.

Embodiments of the composite material can provide excellent physical and chemical behavior due to the equal or highly similar physical and chemical behavior of the first and second materials, such as coefficient of thermal expansion, specific heat capacity, thermal conductivity, chemical compatibility in particular with respect to HPLC requirements, etc. The composite material can be selected to provide an excellent melting composite with no interfuse but fluid tight forming of the first and second materials onto each other, thus showing high sealing between the first and second materials.

The difference in melting point between the first and second materials allows to process the first material during heating to be plastifyable (also referred to as plasticizable) or even liquid like, while the second material is still (at least substantially) solid and remains its shape, thus e.g. keeping a guiding and/or alignment function (for example for one or more further components). The term "plastifyable" as used herein can be understood as a doughy or kneadable transition between solid and liquid state, wherein the plastifyable material can be reformed (i.e. varied in a physical dimension) substantially without destruction of polymer chains and also requiring lower force than in solid state.

Heating the composite material can be provided to seal the first material to the second material. Alternatively or in addition, the first material can be sealed to a further component.

In one embodiment, wherein a further component is to be coupled with the composite material, a body of the second material is provided, and the further component is coupled to (e.g. inserted into) the body of the second material. The composite material is then provided by forming the first material to (e.g. onto) the body of the second material. The coupled further component is sealed (by the first material) to the body of the second material by heating the composite material. Such embodiments allow that, during heating of the composite material, the further component can be positioned with respect to the second material, which still maintains its shape and requirements for positioning the further component, while the first material provides the sealing of the further component.

In another embodiment, wherein also a further component is to be coupled to the composite material, a body of the second material is provided, and the first material is formed to the body of the second material to provide the composite material. The further component is coupled to (e.g. inserted into) the second material within the composite material. Heating the composite material provides sealing (by the first material) of the further component to the body of the second material. Also in this embodiment, the body of the second material allows positioning of the further component and also allows maintaining such positioning requirements even during heating of the composite material for sealing the further component.

The further component might be or comprise a fluid conduit for conducting a fluid, such as a capillary, a light guide configured for guiding light such as an optical fiber, a cavity e.g. as part of complex shape, and/or a cladding and/or casing configured to be attached to or at least partly surround the composite material. Thus, embodiments of the invention allow providing a coupling to very delicate or fragile components, e.g. made of glass, ceramic, etc., which can be positioned as required but also adequately sealed.

The body of the second material may comprise a channel for conducting fluid. Such channel might be coupled with the further component. For example, the channel might open into a fluid conduit or otherwise be fluidically coupled thereto. With the channel being in the second material, its shape and/or dimensions can be maintained even during heating of the composite material for providing the sealing.

Coupling of the further component can be any kind of bringing of the further component in physical contact with the body of the second material and may in particular comprise inserting, attaching, surrounding, and/or positioning the further component with respect to the body of the second material.

In one embodiment, a fluid conduit for conducting fluid is provided, partly surrounded with the first material, and partly surrounded with the second material to provide the composite material. The composite material surrounding the fluid conduit is heated in order to provide sealing between the first material and the fluid conduit. During heating of the composite material, the second material may provide positioning of the fluid conduit while the first material provides the sealing.

In one embodiment, a first portion at an end of the fluid conduit is surrounded with the first material. A second portion of the fluid conduit adjacent to the first portion is surrounded with the second material. Adjacent, in this context, shall mean in an axial direction of the fluid conduit or, in other words, in or against a direction of the fluid flow. A third portion of the fluid conduit adjacent to the second portion is surrounded with the first material. In such embodiment, the second material surrounding the fluid conduit in the first portion may provide a required mechanical stability or positioning of the fluid conduit even during heating for providing the sealing.

The fluid conduit can be made of or comprise a metal, stainless steel, titanium, plastic, polymer, ceramic, glass and/or quartz. The fluid conduit may have a lumen having a diameter of less than 0.8 mm, particularly less than 0.2 mm. The fluid conduit may have circular, elliptical, rectangular or any other suitable shape as known in the art and may also show variations in diameter and/or shaping. The tubing may be or comprise a capillary. The fluid conduit may comprise an inner conduit (e.g. an inner tubing) and an outer conduit (e.g. an outer tubing). The outer conduit surrounds (e.g. radially) the inner conduit. The inner conduit may be comprised of a material different from the outer conduit. The outer conduit may be a socket for adapting to a desired outer diameter for the conduit and/or specific requirements for further tightening elements e.g. ferrules.

In a further embodiment, a fluid conduit configured for conducting fluid is provided of the second material. An end of the fluid conduit (of the second material) is surrounded with the first material, thus providing the composite material. The composite material is heated in order to provide sealing between the first material and the fluid conduit of the second material. Such fluid conduit can provide a biocompatible fluid conduit, with the end-sided first material providing the required sealing.

A cladding, e.g. by a metal material, ceramics, glass or fused silica, may be provided around the composite material, for example only in the range of the end of the fluid conduit (for example as a socket) or around the entire or most of the length of the fluid conduit. The cladding for the composite material might be provided before heating the composite material.

The composite material may be cladded with a material having a thermal expansion coefficient which is substantially equal or larger than a thermal expansion coefficient of the first material, preferably at least in a temperature range below the melting point of the first material and at least down to a lowest temperature required by a respective application, such as room temperature, 0° C. or −40° C. Thus, the cladding may provide a compression force onto the composite material while cooling down and while the materials shrink. This additional force enhances the sealing pressure between the surface areas of contact and provides a long-term stability against settling or creeping of the polymer partner materials. The cladding might be provided by a metal alloy of nickel and titanium, preferably using nitinol, which provides shape-memory and super-elasticity.

While providing the composite material and heating the composite material (to provide sealing by the first material) can be executed in sequential order, this might also result from a single process step. For example, the composite material can be formed and heated concurrently, so that both steps are integrally combined. For example, the composite material can be provided and heated by molding the first material onto the second material.

Forming the first material to the second material can be provided by or comprise any process as known in art, in particular a thermoplastic process, such as injection molding, extrusion, compression molding, remelting and/or transfer molding.

The PAEK materials can be or comprise PEK, PEEK, PEKK, PEEKK, or PEKEKK. Preferred combinations have been found, for example, in PEEK as the first material and PEK or PEKK as the second material. Suitable PAEK-blends, i.e. blends of PAEK and another material, may also be used, e.g. PEEK-blends of e.g. Polyetheretherketone/ Polyetherimid (PEEK/PEI) may be considered e.g. for the first material.

The first and second materials are preferably selected by having a difference in melting points in the range of 10°-100° K, preferably 20°-70° K and more preferably 40°-50° K.

PAEKs may be produced in two ways, one is called the nucleophilic route and the other is called the electrophilic route. The nucleophilic route has the formation of ether linkages in the polymerization step. The electrophilic route has the formation of carbonyl bridges during the polymerization step. The material can be processed using all of the typical thermoplastic processes, such as injection molding, extrusion, compression molding, and transfer molding.

For providing the sealing by the first material, the composite material can be heated to a temperature in the range of the lower melting point of the first material, so that the temperature is close, slightly above, or slightly below the melting point of the first material. Preferably, the temperature is selected below the melting point of the second material. The temperature can be selected where the first material can still be reformed while the second material substantially maintains its shape or requirement for positioning a further component.

Embodiments of the invention provide a sealed fluidic component for use in a fluidic flow path, preferably in an HPLC application. The fluidic component comprises a composite material having first and second materials, with the first material and the second material being different PAEK materials, and the first material having a lower melting point than the second material. The composite material has been heated in order to provide a sealing by the first material.

The sealed fluidic component can be a coupling part of a flow cell. The flow cell is configured for measuring an optical property of a fluid conducted through a fluid conduit. The coupling part is provided for coupling light into the fluid conduit by light guide, coupling out light from the fluid conduit by tight guide, coupling fluid into the fluid conduit, and/or coupling out fluid from the fluid conduit.

The sealed fluidic component can be or comprise a fluid conduit, a fitting or fitting element for coupling a fluid conduit to another device or component, a flow cell, and/or a sensor, for example a sensor for sensing pressure, flow rate and/or temperature, or a part of the sensor.

The terms "fitting" and "fitting element", as used herein, shall both relate to coupling a fluid conduit (e.g. a tubing) to a fluidic device. The term "fitting" shall cover all components required for coupling the fluid conduit to the fluidic device, and may even comprise the fluid conduit and/or the fluidic device, or parts thereof. The term "fitting element" shall cover a part of the fitting.

The fluidic flow path can be a separation flow path configured for separating compounds of a sample fluid comprised in a mobile phase, which can be driven through the separation flow path.

An embodiment of the present invention comprises a fluid separation system configured for separating compounds of a sample fluid in a mobile phase. The fluid separation system comprises a mobile phase drive, such as a pumping system, configured to drive the mobile phase through the fluid separation system. A separation unit, which can be a chromatographic column, is provided for separating compounds of the sample fluid in the mobile phase. The fluid separation system may further comprise a fitting element and/or fitting as disclosed in any of the aforementioned embodiments for coupling a tubing (provided the conducting the mobile phase) to a fluidic device in such fluid separation system. The fluid separation system may further comprise a sample injector configured to introduce the sample fluid into the mobile phase, a detector configured to detect separated compounds of the sample fluid, a collector configured to collect separated compounds of the sample fluid, a data processing unit configured to process data received from the fluid separation system, and/or a degassing apparatus for degassing the mobile phase. The fluidic device to which the tubing is or can be coupled can be any of such devices, and plural of such fittings or fitting elements may be used within such fluid separation system.

Embodiments of the present invention might be embodied based on most conventionally available HPLC systems, such as the AGILENT® 1290 INFINITY® Series system, AGILENT® 1200 Series RAPID RESOLUTION® LC system, or the AGILENT® 1100 HPLC series (all provided by the applicant Agilent Technologies, Inc.—see the website aglient.com—which shall be incorporated herein by reference).

One embodiment comprises a pumping apparatus having a piston for reciprocation in a pump working chamber to compress liquid in the pump working chamber to a high pressure at which compressibility of the liquid becomes noticeable. One embodiment comprises two pumping apparatuses coupled either in a serial (e.g. as disclosed in EP 309596 A1) or parallel manner.

The mobile phase (or eluent) can be either a pure solvent or a mixture of different solvents. It can be chosen e.g. to minimize the retention of the compounds of interest and/or the amount of mobile phase to run the chromatography. The mobile phase can also been chosen so that the different compounds can be separated effectively. The mobile phase might comprise an organic solvent like e.g. methanol or acetonitrile, often diluted with water. For gradient operation water and organic are delivered in separate bottles, from which the gradient pump delivers a programmed blend to the system. Other commonly used solvents may be isopropanol, tetrahydrofuran (THF), hexane, ethanol and/or any combination thereof or any combination of these with aforementioned solvents.

The sample fluid might comprise any type of process liquid, natural sample like juice, body fluids like plasma or it may be the result of a reaction like from a fermentation broth.

The fluid is preferably a liquid but may also be or comprise a gas and/or a supercritical fluid (as e.g. used in supercritical fluid chromatography—SFC—as disclosed e.g. in U.S. Pat. No. 4,982,597 A).

The pressure in the mobile phase might range from 2-200 MPa (20 to 2000 bar), in particular 10-150 MPa (100 to 1500 bar), and more particular 50-120 MPa (500 to 1200 bar).

The HPLC system might further comprise a sampling unit for introducing the sample fluid into the mobile phase stream, a detector for detecting separated compounds of the sample fluid, a fractionating unit for outputting separated compounds of the sample fluid, or any combination thereof. Further details of HPLC systems are disclosed with respect to the aforementioned AGILENT® HPLC series, provided by the applicant Agilent Technologies, Inc. at the website agilent.com which shall be incorporated herein by reference.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in or by the control unit.

BRIEF DESCRIPTION OF DRAWINGS

Other objects and many of the attendant advantages of embodiments of the present invention will be readily appreciated and become better understood by reference to the following more detailed description of embodiments in connection with the accompanying drawing(s). Features that are substantially or functionally equal or similar will be referred to by the same reference sign(s). The illustration in the drawing is schematic.

Figure 1:
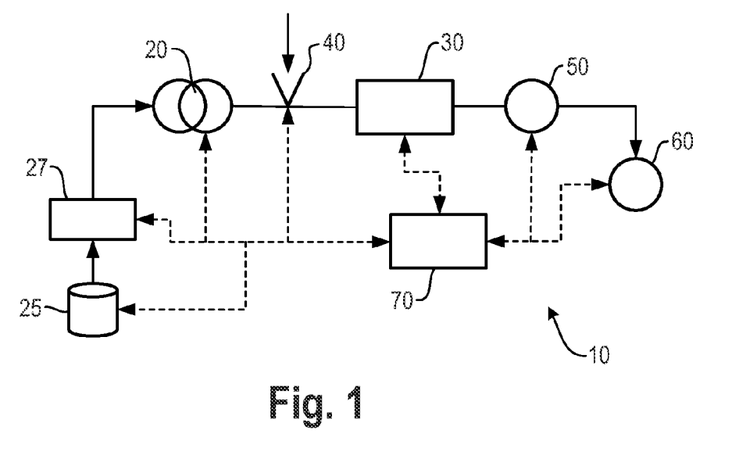
FIG. 1 shows in schematic view a liquid separation system 10, in accordance with embodiments of the present invention, e.g. used in high performance liquid chromatography (HPLC).

Referring now in greater detail to the drawings, FIG. 1 depicts a general schematic of a liquid separation system 10. A pump 20 receives a mobile phase from a solvent supply 25, typically via a degasser 27, which degases and thus reduces the amount of dissolved gases in the mobile phase. The pump 20—as a mobile phase drive—drives the mobile phase through a separating device 30 (such as a chromatographic column) comprising a stationary phase. A sampling unit 40 can be provided between the pump 20 and the separating device 30 in order to subject or add (often referred to as sample introduction) a sample fluid into the mobile phase. The stationary phase of the separating device 30 is configured for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump 20). The data processing unit 70 might also control operation of the solvent supply 25 (e.g. setting the solvent/s or solvent mixture to be supplied) and/or the degasser 27 (e.g. setting control parameters such as vacuum level) and might receive therefrom information regarding the actual working conditions (such as solvent composition supplied over time, flow rate, vacuum level, etc.). The data processing unit 70 might further control operation of the sampling unit 40 (e.g. controlling sample injection or synchronization of sample injection with operating conditions of the pump 20). The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provide data back.

From the example of FIG. 1, it can be seen that the flow path of the mobile phase typically comprises plural individual components, such as pump 20, separating device 30, sampling unit 40, and detector 50, which are coupled together and which might also be comprised of individual sub-components. Also, fluid conduits, e.g. capillaries, for conducting the fluid are provided as indicated by the solid connections in FIG. 1. Coupling of parts, components and fluid conduits, in particular when using exchangeable or modular parts, is usually provided by using fittings as explained in the introductory part of the description.

For transporting liquid within the liquid separation system 10, typically tubings (e.g. tubular capillaries) are used as conduits for conducting the liquid. Fittings are commonly used to couple plural tubings with each other or for coupling a fluid conduit (e.g. a tubing) to any device. For example, fittings can be used to connect respective fluid conduits to an inlet and an outlet of the chromatographic column 30 in a liquid-sealed fashion. Any of the components in the fluid path (solid line) in FIG. 1 may be connected by fluid conduits e.g. using fittings. While the fluid path after the column 30 is usually at lower pressure, e.g. 50 bar or below, the fluid path from the pump 20 to the inlet of the column 30 is under high pressure, currently up to 1200 bar, thus posing high requirements to fluid tight connections.

Due to the high pressure applied in most HPLC applications, pressure sealing of the components in and along the flow path is required. Further, in case of requirement of biocompatibility, it has to be ensured that all surfaces of components (including conduits) along the flow path, which may come in contact with the mobile phase and the sample fluid, are comprised of materials generally considered as being biocompatible, i.e. not releasing ions (e.g. from metal parts) which may contaminate the sample and/or a column packaging material, and/or adversely affect the analysis itself. Accordingly, proper sealing is required to ensure such biocompatibility.

In the following, several exemplary embodiments of components or devices typically used along the fluid flow path in HPLC are shown, which require proper sealing. Each such embodiment has been made by using a composite material comprising two different PAEK materials, one having a lower melting point than the other. Sealing is provided by the PAEK material having the lower melting point when heating the composite material.

Figure 2A:
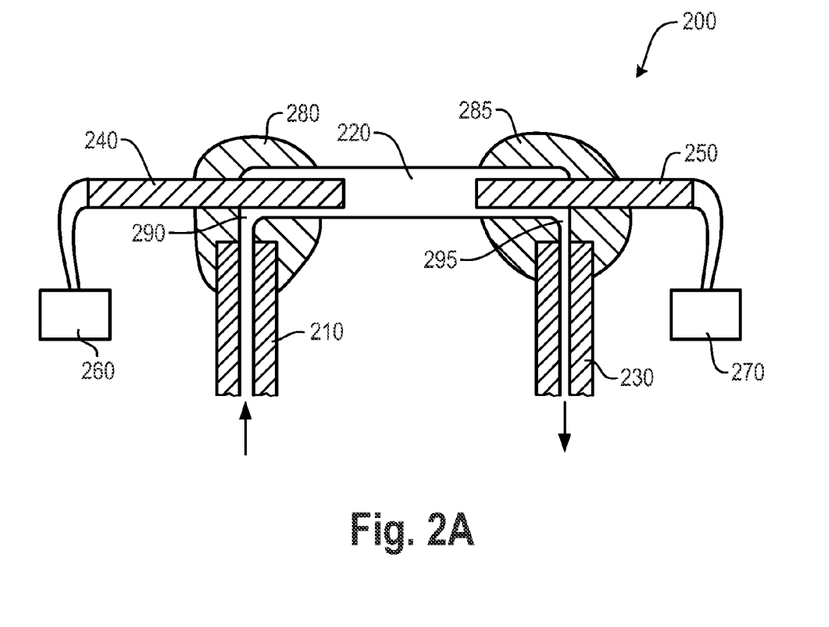
FIG. 2A shows an embodiment of a flow cell 200 configured for measuring an optical property of a fluid.

FIG. 2A shows an embodiment of a flow cell 200 configured for measuring an optical property of a fluid. The flow cell 200 substantially corresponds to the flow cell as disclosed in the aforementioned EP 1910731 A1, and the teaching thereof with respect to flow cells shall be incorporated herein by reference. The flow cell 200 can be the detector 50 or a part thereof.

In FIG. 2A, a first fluid conduit 210 conducts fluid into the flow cell 200 as indicated by the arrow (below the first fluid conduit 210). A second fluid conduit 220 is fluidically coupled with the first fluid conduit 210 and provides a chamber for measuring the optical property of the fluid conducted through the second fluid conduit 220. A third fluid conduit 230 is fluidically coupled with the second fluid conduit 220 and receives fluid therefrom as indicated by the arrow (below the third fluid conduit 230). A first light guide 240 and a second light guide 250 are each interposed from opposite directions into the second fluid conduit 220.

In operation, the first light guide 240 receives an optical signal from a signal source 260 and guides the optical signal into the measuring chamber provided by the second fluid conduit 220. Fluid is flowing from the first fluid conduit 210 through the measuring chamber of the second fluid conduit 220 and into the third fluid conduit 230. The second light guide 250 receives the optical signal, or at least a part thereof, which has been propagated through the fluid, and provides the received optical signal to an optical detector 270. The measuring chamber provided by the second fluid conduit 220 may be configured as a total reflection cell, so that at least most of the optical signal provided by the first light guide 240 will be subject to total reflection when hitting the sidewalls of the second fluid conduit 220 and before entering the second light guide 250. This can be achieved, e.g., by embodying the second fluid conduit 220 as a glass capillary with air surrounding its outer surface, or by using a material having a lower refractive index as the fluid, such as TEFLON® AF material as a family of amorphous fluoropolymers.

In order to provide a fluid tight and sealed coupling of the first, second and third fluid conduits 210, 220, 230 as well as of the light guides 240 and 250, a first coupling part 280 and a second coupling part 285 are provided at each side (e.g. end) of the second fluid conduit 220. The first coupling part 280 comprises a first channel 290 and is configured to provide a fluid tight coupling of the first conduit 210 via the first channel 290 to the second fluid conduit 220. Further, the first coupling part 280 is configured to provide a sealed coupling of the first light guide 240 into the second fluid conduit 220. In operation, fluid flowing from the first fluid conduit 210 is guided via the first channel 290 into the second fluid conduit 220, and the optical signal is coupled into the second fluid conduit 220 by the first light guide 240.

The second coupling part 285 can be embodied substantially similar to or even the same as the first coupling part 280, thus leveraging from a symmetry of this embodiment of the flow cell 200. Accordingly, fluid from the second fluid conduit 220 can flow off via a second channel 295 within the second coupling part 285 and into the third fluid conduit 230.

Due to the symmetrical design of the flow cell 200 in the embodiment of FIG. 2A, it is clear that the direction of flowing in and out of the fluid as well as light guiding in and out can be reversed. The light guide 240, 250 can be any kind of light guide, such as optical fibers. The first and third fluid conduits 210, 230 can be capillaries (e.g. of glass or metal) as commonly used in HPLC. The second fluid conduit 220 can be a capillary (preferably made of glass) and can be selected in shape and size (e.g. length) according to the respective detection requirements.

Figure 2B:
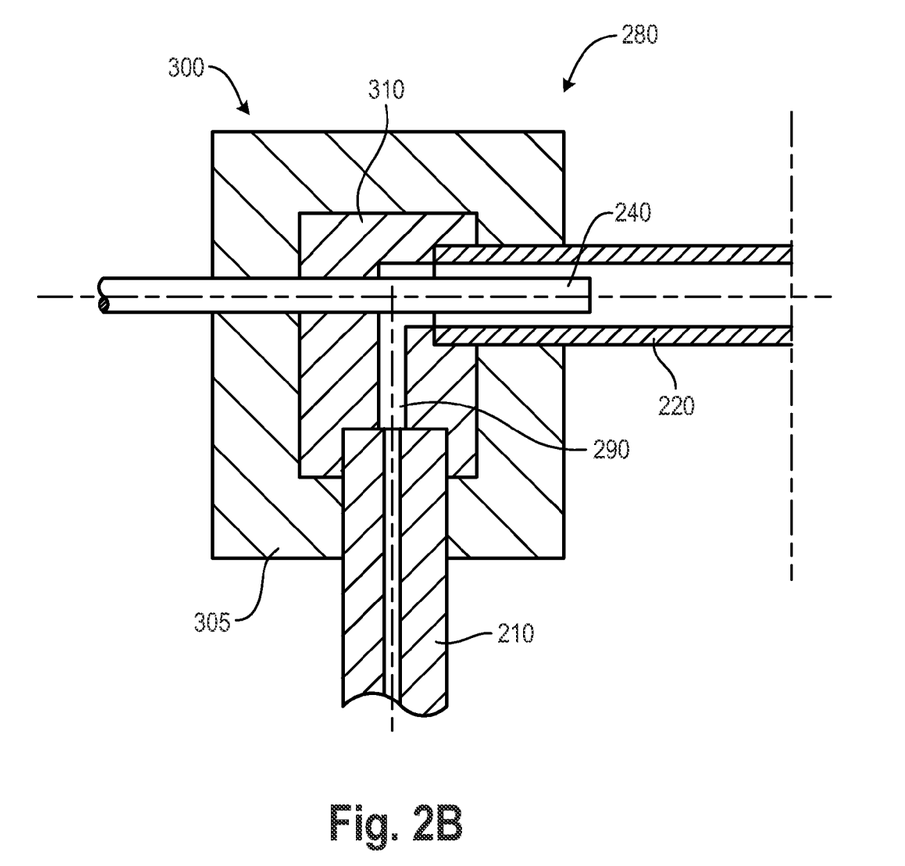
FIG. 2B shows in greater detail an embodiment of a coupling part 280.

FIG. 2B shows in greater detail an embodiment of the coupling part 280 (or correspondingly of the coupling part 285). The embodiment of FIG. 2B is in particular designed to allow a fluid tight and sealed coupling even when using liquid (as the fluid) and in a pressure range of 70 to 500 bar.

The coupling of the first and second fluidic conduits 210, 220 and the light guide 240 is provided by a composite material 300 of a first material 305 and a second material 310. The composite material 300 provides an integral component for sealingly coupling the respective components. Both the first and second materials 305, 310 are composed of a PAEK material, but different from each other, with the first material 305 having a lower melting point than the second material 310. The second material 310 is selected and configured to allow positioning of the respective components 210, 220 and 240 with respect to each other and also to maintain such positioning during the process of manufacturing the coupling part 280 and in particular during a heating process for sealing the components 210, 220 and 240 by the first material 305. The sealing is provided for achieving a fluid tight flow path by the first and second fluid conduits 210 and 220, as well as by the light guide 240 coupling into the second fluid conduit 220. The channel 290 provides a flow path between the first and second fluid conduits 210 and 220 and is part of the flow path to be sealed. The channel 290 is configured in the second material 310 to ensure that its position as well as dimensions are at least substantially maintained during the heating process required for achieving the sealing of the first material 305.

In one embodiment, the process of manufacturing the coupling part 280 of FIG. 2B is accomplished by first forming a body of the second material 310, as indicated by the shape of the second material 310 in FIG. 2B. The body of the second material 310 can be made already containing openings or recesses for receiving the components 210, 220, and 240. Alternatively, such openings or recesses might be applied by an additional step after providing the second material body 310. Accordingly, the channel 290 may be formed during manufacturing of the second material block 310 or thereafter.

The further components of the first fluid conduit 210, the second fluid conduit 220, and the light guide 240 are then inserted into the body of the second material 310. The composite material 300 is derived by forming the first material 305 onto the body of the second material 310 with the further components 210, 220 and 240 being inserted thereto. The composite material 300 is adequately heated so that the inserted further components 210, 220 and 240 are sealed by the first material 305 to the body of the second material 310.

In an alternative embodiment, the body of the second material 310 is provided or formed in accordance with the previous embodiment. In this embodiment, however, the composite material 300 is provided by forming the first material 305 onto the body of the second material 310. The further components 210, 220, 240 are then inserted into the composite material 300 of the first and second materials 305, 310. After inserting, the composite material 300 is adequately heated, thus sealing the inserted further components 210, 220, 240 to the body of the second material 310 by the first material 305.

In the embodiment of FIG. 2B, the first material 305 is selected to be PEEK having a melting point of 343° C., while the second material 310 is selected to be PEK having a melting point of 387° C. Due to the difference in melting point of 44° K, the first material 305 can be processed during heating to be plastifyable or even liquid like, while the second material 310 is still (at least substantially) solid and remains in its shape, thus keeping its guiding and/or alignment function for the further components 210, 220, 240 and also maintaining size and shape of the channel 290.

The composite material 300 is heated or at least partly heated to a temperature in the range of the lower melting point of the first material 305 but kept lower than the melting point of the second material. In this embodiment, the heating temperature for providing the sealing is selected in the range of 340-360° C. In this range of temperature, the first material 305 (PEEK) can still be reformed while the second material 310 (PEK) substantially maintains its shape and requirements for positioning the further components 210, 220, 240.

Forming of the first material 305 to the second material 310 can be provided by any kind of thermoplastic process, in particular a molding process. Accordingly, forming the body of the second material 310 can also be provided by using a thermoplastic process such as molding. By adequately designing the process of forming the first material 305 to the second material 310, the processes of providing and heating the composite material 300 can also be done in one step, for example by directly molding the first material 305 onto the body of the second material 310 with the further components 210, 220, 240 already inserted.

Figure 3A:
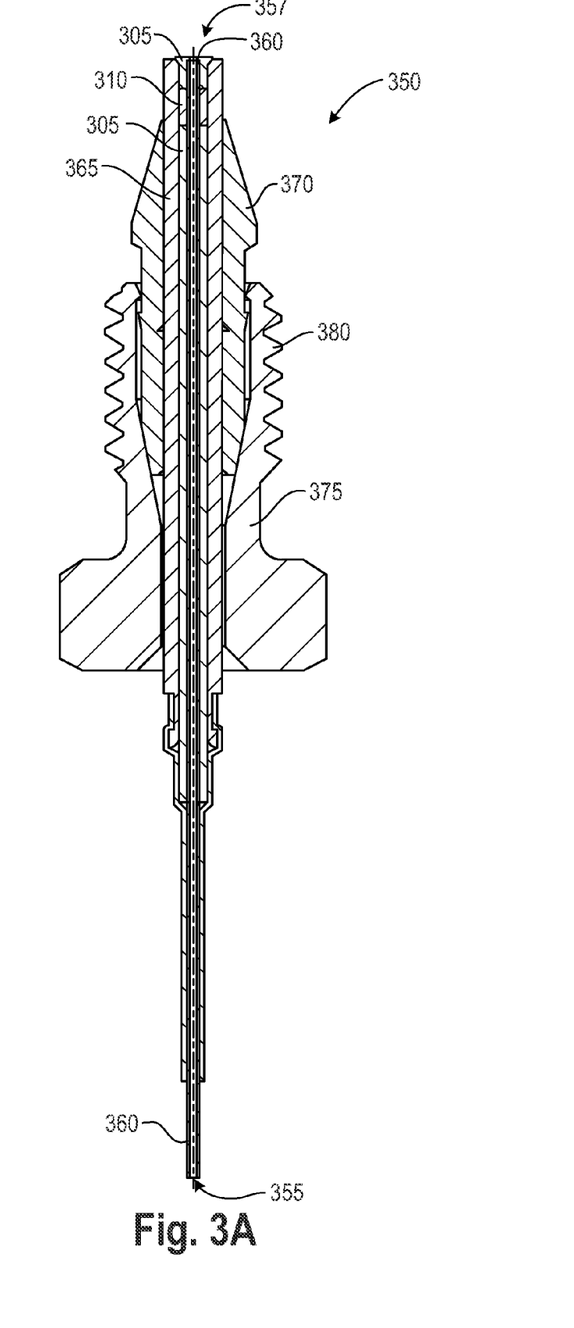
FIGS. 3A and 3B show a different application of a composite material 300 in the context of a fitting 350.

FIG. 3A shows a different application of the composite material 300 in the context of a fitting 350 configured for coupling a fluid conduit 355 at one end side 357 to another device (not shown in the drawings). Further details of fittings can be seen in the respective documents cited in the introductory part of the description. The end side 357 is also shown in greater detail in FIG. 3B.

Figure 3B:
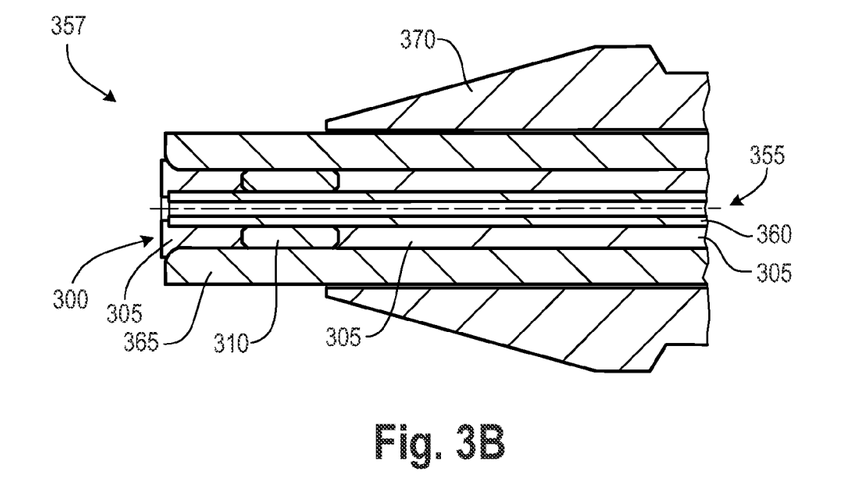

The fluid conduit 355 is provided by an inner conduit 360, such as a capillary, which may be of fused silica, metal such as Stainless Steel (SST), or the second material 310. The inner conduit 360 is surrounded in the region of the end side 357 by the composite material 300 comprising the first material 305 at the front side adjacent to the second material 310, which again is adjacent to a further layer of the first material 305. In other words, a ring of the second material 310 is neighboring layers of the first material 305 on either side in axial direction of the fluid conduit 355.

The fluid conduit 360 surrounded by the composite material 300 may be further surrounded by a cladding 365, which may be of a hard material, such as SST, or even by another layer of the second material 310.

Figure 4A:
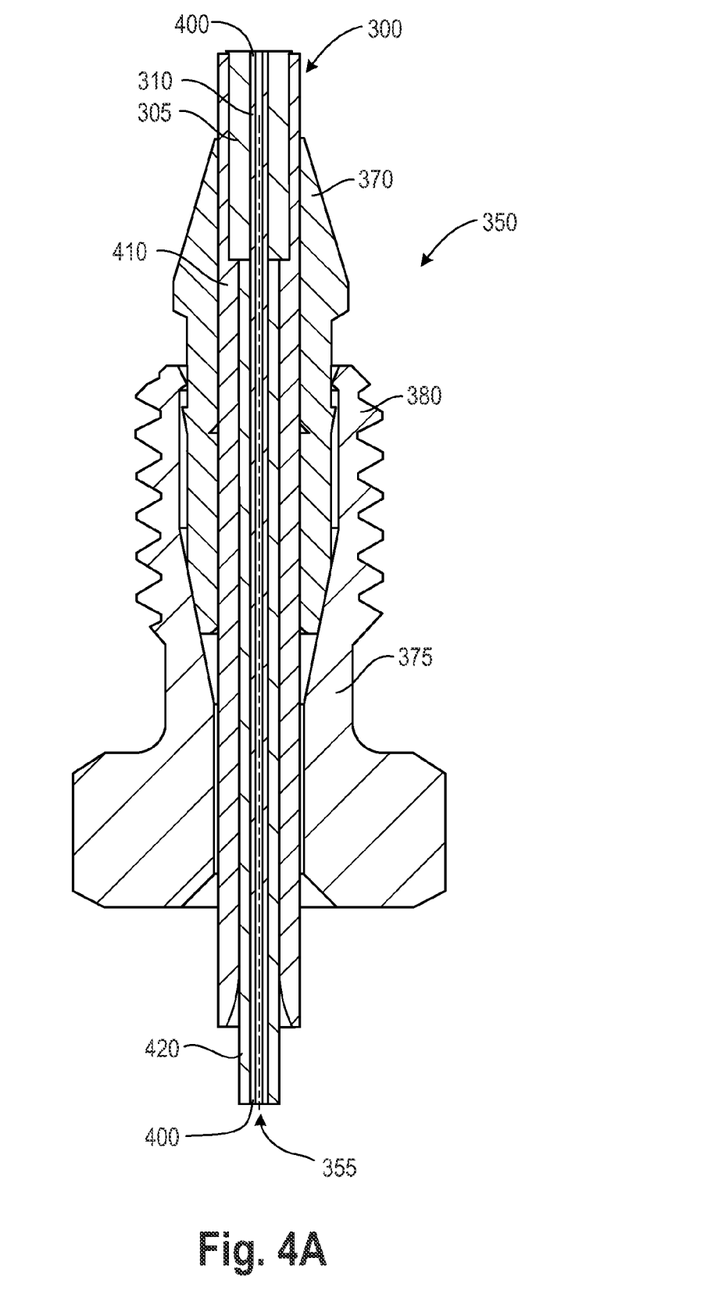
FIGS. 4A and 4B show an alternative embodiment of the composite material 300 in the context of the fitting 350.

The fitting 350, which is placed on top of the fluid conduit 360 at the front sided end 357 of the fluid conduit 360, can be any kind of fitting as known in the art and as described in the introductory part of the description. In the exemplary embodiment of FIGS. 3A and 3B, the fitting 350 comprises a ferrule 370 and a fitting screw 375. The ferrule 370, in the representation of FIGS. 3A and 4A, is shown, for the sake of simplicity, as one piece but can also be of different parts (such as separate front and back ferrules) and different materials. In case of separate front and back ferrules, the front ferrule can be, e.g., a coned subzone located close to the front side end 357, while the back ferrule can be, e.g., an inversely coned subzone at the other end of the ferrule 370. The fitting screw 375 comprises a thread 380. When screwing the fitting screw 375, placed over the ferrule 370, against a counteracting thread component (not shown) of the device to be coupled, the fitting screw 375 will, on one hand, exert a grip force in radial direction onto the ferrule 370 in order to fixedly clamp the ferrule 370 to the fluid conduit 355. On the other hand, screwing the fitting screw 375 will also exert an axial force onto the cladding 365, thus pressing the front sided end 357 against the device it is coupling to. Further details on the fitting and alternative embodiments are readily apparent from the disclosure mentioned in the introductory part of the description.

When adequately heating the composite material 300, surrounding the fluid conduit 360, the ring of the second material 310 will maintain its form stability and still position the cladding 365 with respect to the fluid conduit 360, while the first material 305 will sealingly couple the fluid conduit 360 with the second material 310 as well as with the cladding 365, if provided. The ring of the second material 310 can thus ensure that the fluid conduit 355 can maintain its concentric set up even during and after heating.

Figure 4B:
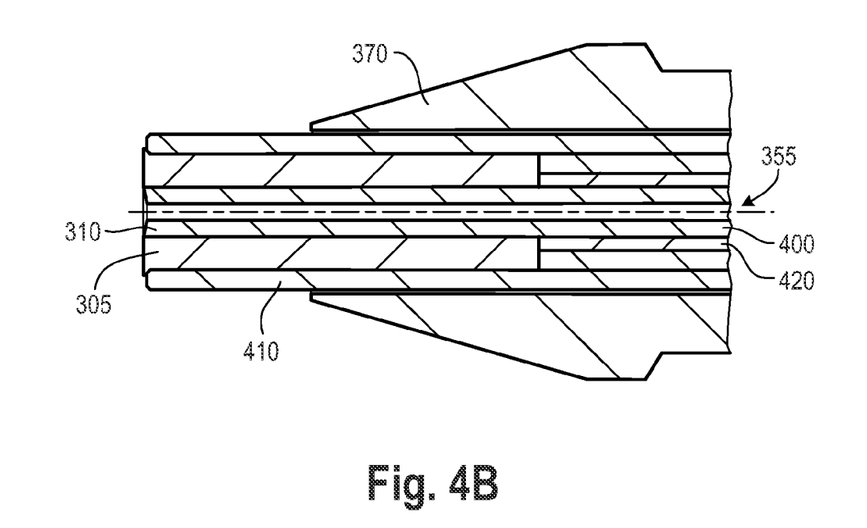

FIGS. 4A and 4B show an alternative embodiment of the fluid conduit 355, with FIG. 4B showing in greater detail the end side to be coupled to a (not shown) other device. As in FIGS. 3A and 3B, the fitting 350 can be employed to couple the fluid conduit 355 to such other device. An inner fluid conduit 400 of the fluid conduit 355 is provided by the second material 310, which in this embodiment may be PEK. At the front sided end, the inner conduit 400 is surrounded by the first material 305, which in this embodiment may be PEEK. The composite material 300 is thus provided at the front sided end of the fluid conduit 355.

In order to increase mechanical stability, the inner conduit 400 may be provided with a cladding 410, which may be limited to only a region at the front sided end of the fluid conduit 355, as shown in the embodiment of FIG. 4A, or which may cover the entirety of the inner conduit 400. The cladding 410 may be of a hard material, such as SST, Nickel-Titanium alloys, and/or fiber-reinforced polymers. Alternatively or in addition, the inner conduit 400 may be surrounded by a coating 420 in order to increase mechanical stability. Such coating 420 may be a metal coating, such as SST, Nickel-Titanium alloys, and/or fiber-reinforced polymers.

When adequately heating the front sided end as depicted in FIG. 4B, the inner conduit 400 of the second material 310 will maintain its shape and form stability, while the first material 305 can provide the required sealing, in particular with respect to the cladding 410 and/or the coating 420. This may also be of importance in particular when requiring biocompatibility.

The invention claimed is:

1. A method of providing a sealed fluidic component for use in a fluidic flow path, the method comprising:
providing a composite material comprising a first material and a second material, wherein the first material and the second material are different PAEK materials with the first material having a melting point lower than a melting point of the second material, and the second material comprises a body comprising an opening or recess for receiving a further component in the opening or recess, the further component comprising a third material is a fluid conduit for conducting fluid;
coupling the further component to the body of the second material in the opening or recess, wherein the second material directly contacts the further component; and
heating the composite material to a temperature in a range of the melting point of the first material and lower than the melting point of the second material, to provide a sealing of the third material of the further component to the body of the second material by the first material,
wherein the first material directly contacts both the further component and the second material, and
wherein the third material is selected from the group consisting of a metal, stainless steel, titanium, a plastic, a polymer, a ceramic, a glass, and quartz.

2. The method of claim 1, wherein providing the composite material, coupling the further component, and heating the composite material comprise, in sequence:
forming the body of the second material;
after forming the body of the second material, coupling the further component;
after coupling the further component, forming the first material onto the body of the second material; and
after forming the first material onto the body of the second material, heating the composite material.

3. The method of claim 1, wherein providing the composite material, coupling the further component, and heating the composite material comprise, in sequence:
forming the body of the second material;
after forming the body of the second material, forming the first material onto the body of the second material;
after forming the first material onto the body of the second material, coupling the further component comprising the third material; and
after coupling the further component, heating the composite material.

4. The method of claim 1, comprising at least one of:
an additional further component comprising a light guide;
the body of the second material comprises a channel for conducting fluid;
coupling the further component comprises at least one of inserting, attaching, surrounding, and positioning the further component comprising the third material with respect to the body of the second material.

5. The method of claim 1, comprising:
providing the composite material comprises partly surrounding the fluid conduit with the first material and partly surrounding the fluid conduit with the second material; and
heating the composite material provides a sealing between the first material and the fluid conduit.

6. The method of claim 5, comprising:
surrounding a first portion of the fluid conduit at an end of the fluid conduit with the first material;
surrounding a second portion of the fluid conduit adjacent, in an axial direction of the fluid conduit, to the first portion with the second material; and
surrounding a third portion of the fluid conduit adjacent, in the axial direction, to the second portion with the first material.

7. The method of claim 5, comprising at least one of:
the fluid conduit has a lumen having a diameter of less than 0.8 mm;
the fluid conduit has a shape selected from the group consisting of a circular shape, an elliptical shape, or a rectangular shape;
the fluid conduit comprises a capillary;
the fluid conduit comprises an inner conduit and an outer conduit, the outer conduit surrounding the inner conduit;
the fluid conduit comprises an inner conduit and an outer conduit, the outer conduit surrounding the inner conduit, the inner conduit being comprised of a different material than the outer conduit;
a socket surrounding the fluid conduit.

8. The method of claim 1, comprising at least one of:
providing the composite material and heating the composite material are executed in one step;
providing the composite material and heating the composite material are executed by molding the first material onto the second material.

9. The method of claim 1, comprising forming the first material to the second material by a thermoplastic process.

10. The method of claim 1, wherein the PAEK materials are selected from the group consisting of PEK, PEEK, PEKK, PEEKK, and PEKEKK.

11. The method of claim 1, comprising at least one of:
the first material is PEEK, and the second material is PEK;
the first material is PEEK, and the second material is PEKK.

12. The method of claim 1, wherein the melting point of the second material is in a range of about 10 K to about 100 K higher than the melting point of the first material.

* * * * *